United States Patent
Van Steenkiste et al.

(10) Patent No.: US 7,133,126 B2
(45) Date of Patent: Nov. 7, 2006

(54) METHOD FOR THE DETECTION OF COATINGS USING EMISSIVITY AND REFLECTIVITY

(75) Inventors: Thomas Hubert Van Steenkiste, Ray, MI (US); Michel F. Sultan, Troy, MI (US); John R. Smith, Birmingham, MI (US)

(73) Assignee: Delphi Technologies, Inc., Troy, MI (US)

( * ) Notice: Subject to any disclaimer, the term of this patent is extended or adjusted under 35 U.S.C. 154(b) by 453 days.

(21) Appl. No.: 10/607,925

(22) Filed: Jun. 27, 2003

(65) Prior Publication Data

US 2004/0263831 A1 Dec. 30, 2004

(51) Int. Cl.
*G01N 21/00* (2006.01)
(52) U.S. Cl. ............ 356/237.1; 165/11.1; 436/37
(58) Field of Classification Search .. 356/237.1–237.5, 356/239.1–239.2; 436/37, 56, 84, 149, 164, 436/172; 165/11.1, 133
See application file for complete search history.

(56) References Cited

U.S. PATENT DOCUMENTS

| | | | |
|---|---|---|---|
| 4,704,603 A | * | 11/1987 | Edwards et al. ............ 340/674 |
| 6,506,605 B1 | | 1/2003 | Allen et al. .................... 436/37 |
| 2003/0066623 A1 | * | 4/2003 | McLean et al. ............ 165/11.1 |
| 2004/0168790 A1 | * | 9/2004 | Hosoe et al. ............... 165/11.1 |

FOREIGN PATENT DOCUMENTS

EP 0300734 A2 * 1/1989

* cited by examiner

*Primary Examiner*—Hoa Q. Pham
(74) *Attorney, Agent, or Firm*—Patrick M. Griffin

(57) ABSTRACT

The subject invention detects the presence of an ozone reducing coating on an automotive radiator of the type having spaced fins presenting electromagnetic surface properties different than the electromagnetic surface properties of the coating. In accordance with the subject invention light rays are emitted or reflected off the coating on the fins to a detector and a comparator compares these light rays to a predetermined benchmark to provide a signal in response to the detected light rays crossing the benchmark. In a species, a second detector is employed to detect rays from an un-coated section to establish the benchmark.

5 Claims, 2 Drawing Sheets

METHOD FOR THE DETECTION OF COATINGS USING EMISSIVITY AND REFLECTIVITY

FIELD OF THE INVENTION

The subject invention relates to an automotive heat exchanger of the type having spaced fins and, more specifically, to the detection of a coating on the fins.

BACKGROUND OF THE INVENTION

The heat exchangers used in automobiles for radiators are coated to reduce the production of ozone from air passing through the passages between the fins of the heat exchanger. It is important to detect the presence and effectiveness of the coating on the vehicle during the useful life of the heat exchanger.

SUMMARY OF THE INVENTION AND ADVANTAGES

The subject invention detects the presence of a coating on a heat exchanger of the type having spaced fins presenting electromagnetic surface properties different than the electromagnetic surface properties of the coating. In accordance with the subject invention electromagnetic rays are issued from the coating on the fins to a detector and a comparator which compares the electromagnetic rays to a predetermined benchmark to provide a signal in response to the rays crossing the benchmark.

Accordingly, the effectiveness of the coating, i.e., the presence of the coating, is continually measured to make sure the coating is reducing the production of ozone. This is accomplished by measuring the optical characteristics of the coating in emissivity and reflectivity, i.e., the electromagnetic properties of the surface of the coating. Accordingly, the primary purpose of the invention is to detect the integrity of the catalytic coating on an automotive heat exchanger for direct ozone reduction.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

The optical reflectivity of a coated surface is a good method for detecting the integrity or delamination of the coating. Therefore, the invention provides a method for detecting the presence of a coating on a heat exchanger of the type having spaced fins having electromagnetic surface properties different than the electromagnetic surface properties of the coating and defining at least one passage between the fins. The electromagnetic surface property is a generic term covering both the reflectivity and the emissivity of the coating. The reflectivity and/or emissivity of the coating material is substantially different from the reflectivity and/or emissivity of the underlying substrate, in this case, the underlying fin.

Figure 1:
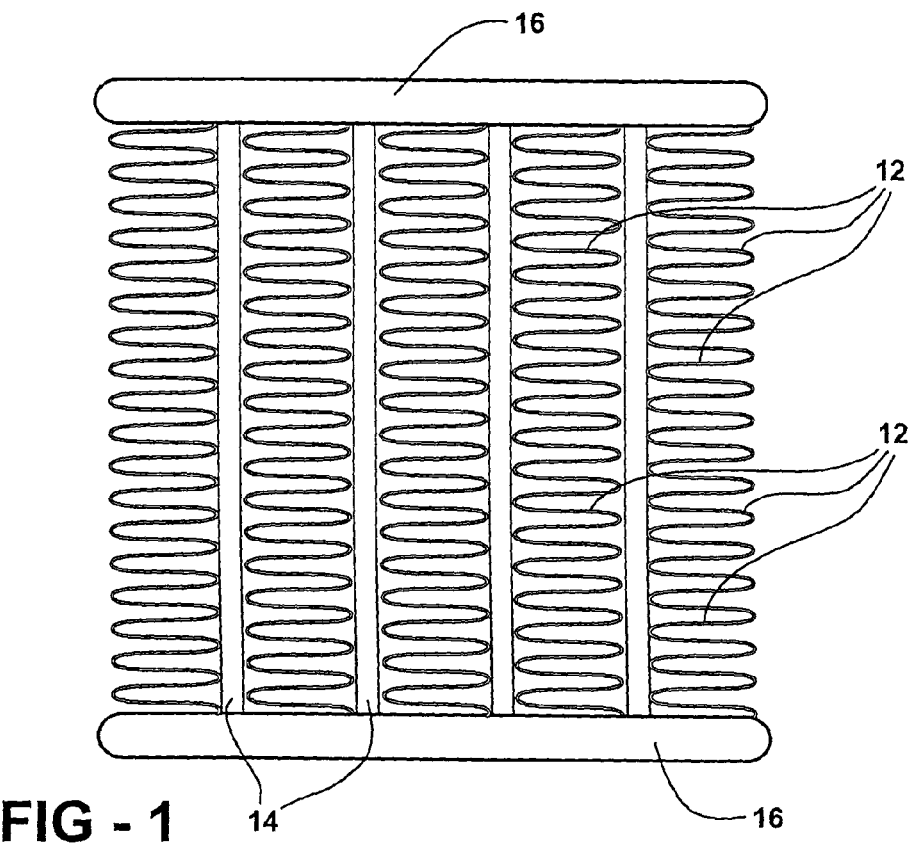
FIG. 1 is a frontal view of a heat exchanger of the type in which the subject invention may be utilized.
Figure 2:
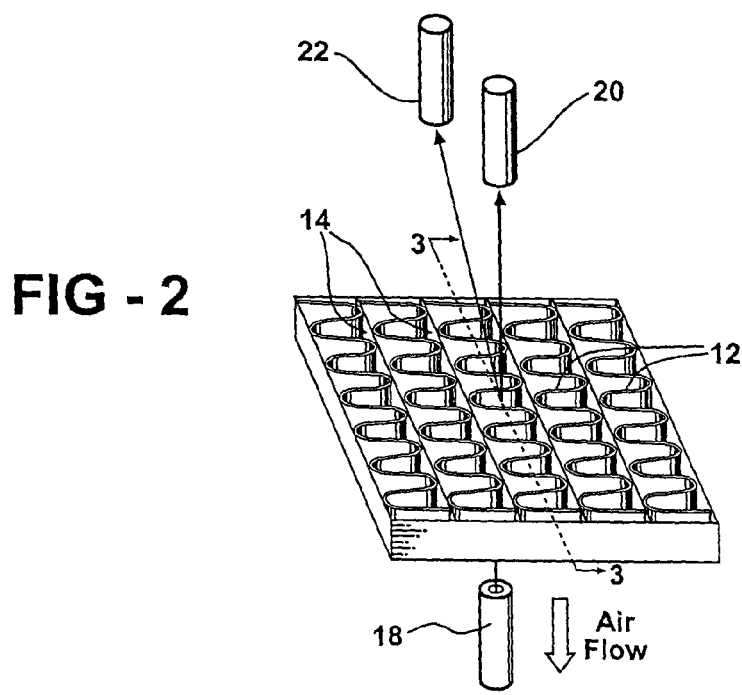
FIG. 2 is a perspective view of the heat exchanger and detection system of the subject invention.
Figure 3:
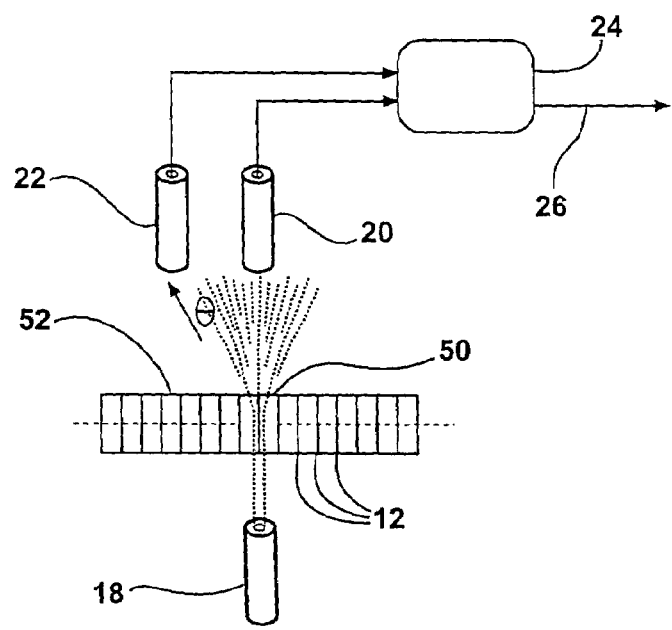
FIG. 3 is a schematic view of the heat exchanger and detection system.
Figure 4:
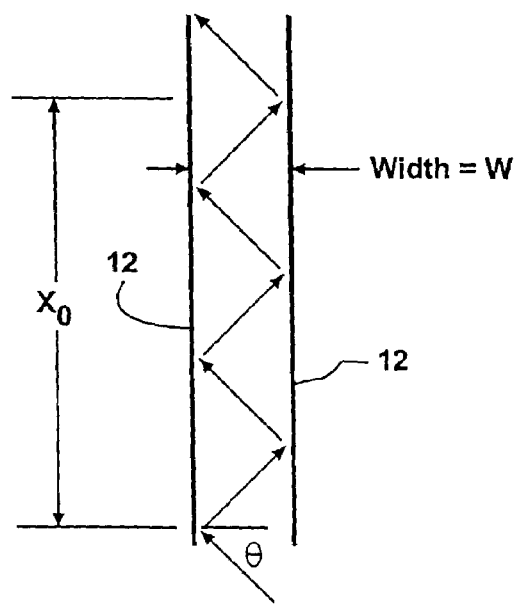
FIG. 4 is a schematic view showing the propagation of the light and the attenuation of the reflected light rays passing through the heat exchanger.

It has been determined that a radiator surface coated with a catalytic layer that converts ozone to oxygen reflects significantly less light than an uncoated radiator surface. In equation form, the reflected light intensity is given by:

$$I(x) = \rho I_0$$

Where I is the light rays from a light source 18, $I_0$ is the incident light, and $\rho$ is the electromagnetic surface properties that depends on the surface. This electromagnetic surface property is higher for an un-coated radiator surface than for a coated one. The ratio of the reflected signal to the incident signal is a ratio of the two electromagnetic surface properties, and, accordingly, is an indicator of the surface characteristics. The effect can be substantially enhanced if the light signal bounces off the surface more than once. This, for example, can be obtained if light is propagated in a waveguide structure such as a passage defined between adjacent fins 12 in a heat exchanger assembly. Such a heat exchanger assembly is shown in FIG. 1 in the form of an automotive radiator of the type including spaced fins 12. The fins 12 are supported on tubes 14 that extend between headers 16 and the fins 12 define a plurality of passages between the fins 12. The fins 12 are coated with an ozone reducing coating having a electromagnetic surface property, e.g., reflectivity, that is lower than the electromagnetic surface property-reflectivity-of the un-coated fins 12. Each of the passages between adjacent fins 12, defines a waveguide structure as illustrated in FIG. 4.

The effective or used length of the waveguide is $x_0$ and the width is w. The planar arrangement is used for simplicity and without loss of generality, even though the fin 12 walls in the radiator are not parallel. The surface of the waveguide is coated with a material of reflectivity $\rho(\lambda)$. A specific guided mode is denoted by a ray with incident angle $\theta$. This guided mode or ray experiences a number of internal reflections N given by:

$$N \cong \frac{x}{w \tan(\theta)}$$

where x is the longitudinal distance traveled by the ray. If the intensity of the incident ray at angle $\theta$ is $I_0(\theta)$, then the intensity of the guided ray is reduced by a factor given by:

$$\frac{I(x)}{I_0} \cong \rho^{\left(\frac{x}{w\tan\theta}\right)} = e^{\left(\frac{-\beta x}{w\tan\theta}\right)} \quad \beta = -\ln(\rho)$$

This reduction factor is significantly more pronounced than for the case of a single bounce.

Most optical sources generate a diverging light beam, which upon entrance into the waveguide, i.e., passage between fins 12, generates a number of modes that propagate at different incidence angles. In this case, the above relationship must be integrated over all propagation modes in order to provide the correct relationship:

$$I(x) \cong \int I_0(\theta) e^{(-\beta x/w \, \tan \, \theta)} d\theta$$

In the above relationships, the lower order propagation modes that are parallel to the fin walls (θ~90°) will bounce much less than the higher order modes, and accordingly, are much less attenuated. Two detectors 20 and 22 are configured such as to capture the lower order and higher order modes respectively, then the signal detected by the first detector 20 will be much less affected by the wall surface than the signal detected by the second detector 22. Accordingly, the first detector 20 can be used as a reference signal to the second detector 22. The normalized or comparative signal of the second detector 22 to the first detector 20 would then be significantly affected by the wall reflectivity, and much less affected by the intensity of the light source 18.

It has been determined that the signal for the case of a coated radiator is less than the signal of an un-coated radiator, indicating a smaller reflection coefficient. The higher order modes attenuate faster for the case of the coated radiator as compared to the un-coated one.

The effects of ambient light can be eliminated through the use of a frequency modulated light source 18, e.g. a light emitting diode excited with an AC signal.

In accordance with the invention, a coating is disposed on the fins 12 and has a reflection coefficient different than the reflection coefficient of the bare or otherwise undercoated fins 12, i.e., different electromagnetic surface properties. The light source 18 propagates light rays through the passage between the fins 12 for reflecting at least some of the light rays off the coating on the fins 12.

The second detector 22 detects reflected light rays reflected off the coaxing and a comparator 24 compares the reflected light rays to a predetermined benchmark for the reflected light rays and provides a signal 26 in response to the reflected light rays crossing the benchmark. In the case where the detector 22 detects emissivity, there would be no light source 18 and the second detector 22 would look at a coated section 50 and the first detector 22 would look at an un-coated section 52. The comparator 24 may include a computer that stores a benchmark value which, when crossed, indicates that the coating is ineffective. This could be accomplished with the second detector 22 alone. Alternatively, it could be accomplished by including the first detector 20 for detecting direct light rays passing through the passage from the light source 18 without reflecting off the fins 12. In this case, the comparator 24 is responsive to the first 20 and second 22 detectors for comparing the reflected light rays to the direct light rays to measure the ratio therebetween. In this manner, the changing brightness of the light source 18 would not affect the measurement of the coating. As alluded to above, the fins 12 could include an un-coated or bare section 52 and the first detector 20 would detect the un-coated light rays reflecting off the un-coated section 52. The comparator 24 would then be responsive to The first 20 and second 22 detectors for comparing the light rays reflected from the coating 50 to the light rays reflected from the un-coated section 52 to measure the ratio therebetween. Or in the case of detecting emissivity, the comparator 24 would then be responsive to the first 20 and second 22 detectors for comparing the light rays emitted from the coating 50 to the light rays emitted from the un-coated section 52 to measure the ratio therebetween. In the emissivity approach, the second detector 22 would view the coated section 50 of the heat exchanger, and the first detector 20 would view the un-coated section 52 as a reference. The emissivity of the coating on the coated section 50 is significantly higher than the emissivity of the bare material 52 of the heat exchanger.

The optical emissivity ($\epsilon$) (for a fixed wavelength range) of different objects depends significantly on material composition, the uniformity of the object's temperature, and surface temperature. The optical reflectivity ($\rho$) of a material is related to its emissivity according to the formula: $\rho = 1 - \epsilon$.

Different materials have been considered as catalytic coatings on the surface of radiators for the purpose of direct ozone reduction as well as different methods of depositing these coatings, including slurries and thermal or kinetic spray processes. In general, the surface texture of the deposited coatings is much rougher than the aluminum, which is the base material of most radiator (heat exchanger) fins. Accordingly, the addition of the coating on the surface of the radiator increases the emissivity and reduces the reflectivity significantly as compared to the base material of the radiator (heat exchanger). If the coating delaminates, the emissivity and reflectivity will be restored to their original values.

All objects radiate energy into a surrounding hemisphere as a function of $$W_B = \sigma T^4$$

where $W_B$=radiated power (W/cm²), $\sigma$=Stefan-Boltzmann constant and T is the temperature in Kelvin of the object. While this equation applies to a perfect blackbody, for objects in the real world another equation must be used:

$$W_B = \epsilon \sigma T^4$$

where the emissivity $\epsilon$ is defined as the ratio of the actual emitted radiance, W, to the theoretical radiation of a perfect blackbody, $\epsilon = W/W_B$. This emissivity is noted as a single number between 0 and 1 (the emissivity of a perfect blackbody=1).

The Forward looking infrared (FLIR) System ThermoCam PM595 was used to detect the presence of a coating on a radiator substrate. The FLIR ThermoCam PM595 camera uses an uncooled microbolometer to detect infrared radiation. For an object at uniform temperature having areas of different emissivities, (i.e., coated and uncoated areas) the infrared camera will see a false temperature difference between the coated and uncoated locations even though they are at the same temperature. In normal operation, one would require uniform emissivity across the area of interest observed by the infrared camera to measure an accurate temperature. Here, this feature is exploited to detect areas of coated and un-coated substrate.

Accordingly, an optical device that measures and tracks with time the electromagnetic surface properties, either the emissivity or the reflectivity, of the material forms the basis of a catalytic coating sensor.

As will be apparent from the foregoing, the invention provides a method far detecting the presence of a coating on a beat exchanger of the type having spaced fins 12 having a electromagnetic surface properties different than the electromagnetic surface properties of the coating and defining at least one passage between the fins 12 wherein the method comprises the steps of detecting electromagnetic rays from the coating, establishing a predetermined benchmark for the electromagnetic rays, comparing 24 the electromagnetic rays to the benchmark, and providing a signal 26 in response to the electromagnetic rays crossing the benchmark.

The method may be perfected by propagating light rays from a light source 18 through the passage between fins 12 and reflecting at least some of the light rays off the coating on the fins 12. The light may be ambient or from a light source, such as a light emitting diode. The method includes detecting reflected light rays reflected off the coating, establishing a predetermined benchmark for the emitted or reflected light rays, and comparing the light rays to the benchmark to provide a signal 26 in response to the light rays crossing the benchmark. The method may include the step of detecting direct light rays passing through the passage from the source without reflecting off the fins 12 and establishing the predetermined benchmark by comparing the emitted or reflected light rays to the direct light rays to measure the ratio therebetween. The method may be perfected by measuring emissivity by detecting at least some of the light rays emitted from a coated section of the fins 12, detecting the un-coated light rays emitted from the un-coated section, and establishing the predetermined benchmark by comparing the light rays emitted from the coating to the light rays emitted from the un-coated section to measure the ratio therebetween.

Obviously, many modifications and variations of the present invention are possible in light of the above teachings. The invention may be practiced otherwise than as specifically described within the scope of the appended claims.

What is claimed is:

1. A method for detecting the presence of a coating on spaced fins having electromagnetic surface properties different than the electromagnetic surface properties of the coating and defining at least one passage between the fins, said method comprising the steps of;

propagating electromagnetic rays from a light source through the passage between fins, establishing a predetermined benchmark for the reflected electromagnetic rays with a first detector, reflecting at least some of the electromagnetic rays off the coating on the fins, detecting reflected electromagnetic rays reflected off the coating with a second detector, comparing the reflected electromagnetic rays from the coating to the benchmark, and providing a signal in response to the reflected electromagnetic rays crossing the benchmark, wherein the step of establishing the predetermined benchmark is further defined as detecting direct electromagnetic rays passing through the passage from the source without reflecting off the fins with the first detector and comparing the reflected electromagnetic rays to the direct electromagnetic rays to measure the ratio therebetween.

2. A method as set forth in claim 1 wherein the step of propagating of electromagnetic rays is further defined as propagating a frequency modulated light.

3. A heat exchanger assembly comprising;

spaced fins having electromagnetic surface properties and defining at least one passage between the fins, a coating on said fins having electromagnetic surface properties different than the electromagnetic surface properties of said fins, a light source for propagating electromagnetic rays through said passage between said fins for reflecting at least some of the electromagnetic rays off said coating said fins, a first detector that detects direct electromagnetic rays passing through the passage from said light source without reflecting off said fins for establishing a predetermined benchmark for the electromagnetic rays;

a second detector for detecting reflected electromagnetic rays from said coating, and a comparator that is responsive to said first and second detectors for comparing the reflected electromagnetic rays to the direct electromagnetic rays to measure the ratio therebetween and providing a signal in response to the ratio crossing the predetermined benchmark.

4. An assembly as set forth in claim 3 wherein said light source comprises a frequency modulated light.

5. An assembly as set forth in claim 3 wherein said light source comprises a light emitting diode.

* * * * *